(12) United States Patent
Harbron et al.

(10) Patent No.: US 7,651,875 B2
(45) Date of Patent: Jan. 26, 2010

(54) CATALYSTS

(75) Inventors: Stuart Harbron, Berkharnsted (GB);
Michael Dov Hammer, Portland, OR (US); Larissa Jangidze, Tbilisi (GE); Avto Tavkhelidze, Tbilisi (GE)

(73) Assignee: Borealis Technical Limited (GI)

( * ) Notice: Subject to any disclaimer, the term of this patent is extended or adjusted under 35 U.S.C. 154(b) by 929 days.

(21) Appl. No.: 11/196,365

(22) Filed: Aug. 2, 2005

(65) Prior Publication Data

US 2005/0281996 A1    Dec. 22, 2005

Related U.S. Application Data

(60) Continuation-in-part of application No. 10/508,914, filed as application No. PCT/US03/08907 on Mar. 24, 2003, now Pat. No. 7,074,498, application No. 11/196,365, which is a continuation-in-part of application No. 10/760,697, filed on Jan. 19, 2004, which is a division of application No. 09/634,615, filed on Aug. 5, 2000, now Pat. No. 6,680,214, which is a continuation of application No. 09/093,652, filed on Jun. 8, 1998, now abandoned.

(60) Provisional application No. 60/366,563, filed on Mar. 22, 2002, provisional application No. 60/366,564, filed on Mar. 22, 2002, provisional application No. 60/373,508, filed on Apr. 17, 2002, provisional application No. 60/149,805, filed on Aug. 18, 1999.

(30) Foreign Application Priority Data

Aug. 2, 2004    (GB) .................. 0417190.6

(51) Int. Cl.
*B32B 15/00*    (2006.01)

(52) U.S. Cl. .............. 438/20; 257/10; 257/E21.09

(58) Field of Classification Search ............ 257/40, 257/10, E29.07, E21.09; 428/209, 426; 438/3, 438/20, 962
See application file for complete search history.

(56) References Cited

U.S. PATENT DOCUMENTS

| | | | |
|---|---|---|---|
| 3,740,592 A | 6/1973 | Engdahl et al. | |
| 4,011,582 A | 3/1977 | Cline et al. | |
| 4,039,352 A | 8/1977 | Marinescu | |
| 4,063,965 A | 12/1977 | Cline et al. | |
| 4,686,162 A | 8/1987 | Stangl et al. | |
| 5,023,671 A | 6/1991 | DiVincenzo et al. | |
| 5,068,535 A | 11/1991 | Rabalais | |
| 5,119,151 A | 6/1992 | Onda | |
| 5,229,320 A | 7/1993 | Ugajin | |

(Continued)

FOREIGN PATENT DOCUMENTS

JP    4080964 A    3/1992

(Continued)

OTHER PUBLICATIONS

Chou et al., Imprint Lithography with 25 Nanometer Resolution, Science, Apr. 5, 1996, pp. 85-87, vol. 272.

(Continued)

*Primary Examiner*—Roy K Potter

(57) ABSTRACT

Nanostructured surface materials having patterned indents are disclosed and there use for catalytic, therapeutic, herbicidal, pesticidal, antiviral, antibacterial and antifungal applications is disclosed.

13 Claims, 1 Drawing Sheet

U.S. PATENT DOCUMENTS

| | | | |
|---|---|---|---|
| 5,233,205 A | 8/1993 | Usagawa et al. | |
| 5,247,223 A | 9/1993 | Mori et al. | |
| 5,332,952 A | 7/1994 | Ugajin et al. | |
| 5,336,547 A | 8/1994 | Kawakita et al. | |
| 5,371,388 A | 12/1994 | Oda | |
| 5,432,362 A | 7/1995 | Lippens et al. | |
| 5,503,963 A | 4/1996 | Hifano | |
| 5,521,735 A | 5/1996 | Shimizu et al. | |
| 5,579,232 A | 11/1996 | Tong et al. | |
| 5,604,357 A | 2/1997 | Hori | |
| 5,654,557 A | 8/1997 | Taneya et al. | |
| 5,675,972 A | 10/1997 | Edelson | |
| 5,699,668 A | 12/1997 | Cox | |
| 5,719,407 A | 2/1998 | Ugajin | |
| 5,722,242 A | 3/1998 | Edelson | |
| 5,772,905 A | 6/1998 | Chou | |
| 5,917,156 A | 6/1999 | Nobori et al. | |
| 5,962,566 A | 10/1999 | Grandfils et al. | |
| 6,117,344 A | 9/2000 | Cox et al. | |
| 6,214,651 B1 | 4/2001 | Cox | |
| 6,225,205 B1 | 5/2001 | Kinoshita | |
| 6,281,514 B1 | 8/2001 | Tavkhelidze | |
| 6,417,060 B2 | 7/2002 | Tavkhelidze et al. | |
| 6,495,843 B1 | 12/2002 | Tavkelidze | |
| 6,531,703 B1 | 3/2003 | Tavkhelidze | |
| 6,680,214 B1 | 1/2004 | Tavkhelidze et al. | |
| 6,962,823 B2 * | 11/2005 | Empedocles et al. | 438/3 |
| 7,074,498 B2 * | 7/2006 | Tavkhelidze et al. | 428/687 |
| 7,220,984 B2 * | 5/2007 | Tavkhelidze et al. | 257/10 |
| 7,288,419 B2 * | 10/2007 | Naya | 438/20 |
| 7,507,987 B2 * | 3/2009 | Kim et al. | 257/10 |
| 2001/0046749 A1 | 11/2001 | Tavkhelidze et al. | |
| 2002/0034474 A1 | 3/2002 | Sabel et al. | |
| 2003/0064965 A1 | 4/2003 | Richter | |
| 2003/0068431 A1 | 4/2003 | Taliashvili et al. | |
| 2003/0152636 A1 | 8/2003 | Sabel et al. | |
| 2004/0007241 A1 | 1/2004 | Li et al. | |
| 2004/0025895 A1 | 2/2004 | Li et al. | |
| 2004/0028812 A1 | 2/2004 | Wessels et al. | |
| 2004/0082521 A1 | 4/2004 | Singh | |
| 2004/0132269 A1 | 7/2004 | Zhang et al. | |

FOREIGN PATENT DOCUMENTS

| | | |
|---|---|---|
| WO | WO 99/13562 A1 | 3/1999 |
| WO | WO 99/40628 A1 | 8/1999 |
| WO | WO 99/47980 A1 | 9/1999 |
| WO | WO 99/64642 A | 12/1999 |
| WO | WO 03/083177 A3 | 10/2003 |

OTHER PUBLICATIONS

Electronic Engineering Times, "Single-electron circuits move beyond . . . Next-generation design rules", Feb. 23, 1998, p. 43, CMP Publicatons.

* cited by examiner

CATALYSTS

CROSS-REFERENCE TO RELATED APPLICATIONS

This application claims the benefit of U.K. Provisional Application No. GB0417190.6, filed Aug. 2, 2004. This application is also a continuation-in-part application of application Ser. No. 10/508,914 filed Sep. 22, 2004 now U.S. Pat. No. 7,074,498, which is a U.S. national stage application of International Application PCT/US03/08907, filed Mar. 24, 2003, which international application was published on Oct. 9, 2003, as International Publication WO03083177 in the English language. The International Application claims the benefit of U.S. Provisional Application No. 60/366,563, filed Mar. 22, 2002, U.S. Provisional Application No. 60/366,564, filed Mar. 22, 2002, and U.S. Provisional Application No. 60/373,508, filed Apr. 17, 2002. This application is also a continuation-in-part application of application Ser. No. 10/760,697 filed Jan. 19, 2004 which is a divisional application of application Ser. No. 09/634,615, filed Aug. 5, 2000, now U.S. Pat. No. 6,680,214, which claims the benefit of U.S. Provisional Application No. 60/149,805, filed on Aug. 18, 1999, and is a continuation application of application Ser. No. 09/093,652, filed Jun. 8, 1998, now abandoned, and is related to application Ser. No. 09/020,654, filed Feb. 9, 1998, now U.S. Pat. No. 6,281,514. The above-mentioned patent applications are assigned to the assignee of the present application and are herein incorporated in their entirety by reference.

BACKGROUND OF THE INVENTION

The present invention relates to catalysis, sensors, and therapeutics.

Small metal aggregates show strong catalytic activity, unknown for bulk structures with identical chemical composition. The distinct absorption behavior of metal clusters provides a basis for various optical applications. The characteristic properties of matter in the atom-to-bulk transition range partly result from a strong size dependence of the electronic structure. The discrete energy levels of isolated atoms split and broaden to electron bands in larger aggregates. The band structure determines the propagation and mobility of electrons inside the crystal. In principle, control over the size-dependent electronic structure allows an adjustment of intrinsic material properties to the demands of a wide range of applications.

The high electron density and efficient screening in metals make the critical length scale for the atom-to-bulk-transition considerably smaller than for semiconductors. Gradual development of metallic behavior has been observed for ultra small clusters, either in the gas phase or on surfaces. The transition is characterized by the closure of gaps in the electronic states and the development of collective electronic excitations.

For example, as the metal particle size decreases, the core-level binding energy of metals such as Au, Ag, Pd, Ni and Cu increases sharply. This increase in the core-level binding energy in small particles occurs due to the poor screening of the core-hole and is a manifestation of the size-induced metal-nonmetal transition. Similarly, the interaction of oxygen with silver nanoclusters has shown the ability of the smaller nanocrystals to dissociate dioxygen to atomic oxygen species. Gold nanoclusters on titania are known to catalyze CO oxidation at a cluster size of around 3.5 nm, with the gold behaving more as a non-metal and smaller cluster sizes.

This change is because the average electronic energy spacing of successive quantum levels, $\delta$, known as the Kubo gap is given by $4E_F/3n$, where $E_F$ is the Fermi energy of the bulk material and n is the total number of valence electrons in the nanocrystal. So for an individual silver nanoparticle of 3 nm diameter containing approximately 1000 silver atoms, the value of $\delta$ is 5-10 meV. Since the thermal energy at room temperature, $kT \approx 25$ meV, a 3 nm particle would be metallic. At lower temperatures, the level spacings become comparable to kT and rendering them non-metallic. Because of the presence of the Kubo gap in individual nanoparticles, properties such as electrical conductivity and magnetic susceptibility exhibit quantum size effects. The resultant discreteness of energy levels also brings about fundamental changes in the characteristic spectral features of the nanoparticles, especially those related to the valence band.

The use of nanoparticles as catalysts has been disclosed in the following: US20040132269, US20040028812, US20040025895, and US20040007241.

A number of applications have been described for the delivery of drugs to targets via the use of nanoparticles (see, for example, U.S. Pat. No. 5,962,566, US20040082521, US 20030152636, US20030064965, and US20020034474).

In U.S. Pat. Nos. 6,281,514, 6,531,703 and 6,495,843 and WO9940628 a method is disclosed for promoting the passage of elementary particles at or through a potential barrier comprising providing a potential barrier having a geometrical shape for causing de Broglie interference between said elementary particles. In another embodiment, the invention provides an elementary particle-emitting surface having a series of indents. The depth of the indents is chosen so that the probability wave of the elementary particle reflected from the bottom of the indent interferes destructively with the probability wave of the elementary particle reflected from the surface. This results in the increase of tunneling through the potential barrier. When the elementary particle is an electron, then electrons tunnel through the potential barrier, thereby leading to a reduction in the effective work function of the surface. In further embodiments, the invention provides vacuum diode devices, including a vacuum diode heat pump, a thermionic converter and a photoelectric converter, in which either or both of the electrodes in these devices utilize said elementary particle-emitting surface. In yet further embodiments, the invention provides devices in which the separation of the surfaces in such devices is controlled by piezo-electric positioning elements. A further embodiment provides a method for making an elementary particle-emitting surface having a series of indents In U.S. Pat. No. 6,117,344 and WO9947980 methods are described for fabricating nano-structured surfaces having geometries in which the passage of elementary particles through a potential barrier is enhanced. The methods use combinations of electron beam lithography, lift-off, and rolling, imprinting or stamping processes.

In U.S. Pat. No. 6,680,214 a method is disclosed for the induction of a suitable band gap and electron emissive properties into a substance, in which the substrate is provided with a surface structure corresponding to the interference of electron waves. Lithographic or similar techniques are used, either directly onto a metal mounted on the substrate, or onto a mold which then is used to impress the metal. In a preferred embodiment, a trench or series of nano-sized trenches are formed in the metal.

In WO03/083177, the use of electrodes having a modified shape and a method of etching a patterned indent onto the surface of a modified electrode, which increases the Fermi energy level inside the modified electrode, leading to a decrease in electron work function is disclosed. The method comprises creating an indented or protruded structure on the surface of a metal. The depth of the indents or height of protrusions is equal to a, and the thickness of the metal is Lx+a. The minimum value for a is chosen to be greater than the surface roughness of the metal. Preferably the value of a is chosen to be equal to or less than Lx/5. The width of the indentations or protrusions is chosen to be at least 2 times the value of a. Typically the depth of the indents is $\geq \lambda/2$, wherein $\lambda$ is the de Broglie wavelength, and the depth is greater than the surface roughness of the metal surface. Typically the width of the indents is $\gg \lambda$, wherein $\lambda$ is the de Broglie wavelength. Typically the thickness of the is a multiple of the depth, preferably between 5 and 15 times said depth, and preferably in the range 15 to 75 nm. FIG. 1 shows the shape and dimensions of a modified electrode having a thin metal film 40 on a substrate 42. Indent 44 has a width b and a depth a relative to the height of metal film 40. Film 40 comprises a metal whose surface should be as plane as possible as surface roughness leads to the scattering of de Broglie waves. Metal film 40 is given sharply defined geometric patterns or indent 44 of a dimension that creates a De Broglie wave interference pattern that leads to a decrease in the electron work function, thus facilitating the emissions of electrons from the surface and promoting the transfer of elementary particles across a potential barrier. The surface configuration of the modified electrode may resemble a corrugated pattern of squared-off, "u"-shaped ridges and/or valleys. Alternatively, the pattern may be a regular pattern of rectangular "plateaus" or "holes," where the pattern resembles a checkerboard. The walls of indent 44 should be substantially perpendicular to one another, and its edges should be substantially sharp. The surface configuration comprises a substantially plane slab of a material having on one surface one or more indents of a depth approximately 5 to 20 times a roughness of said surface and a width approximately 5 to 15 times said depth. The walls of the indents are substantially perpendicular to one another, and the edges of the indents are substantially sharp.

BRIEF SUMMARY OF THE INVENTION

In accordance with one embodiment of the present invention, there is provided a method for catalyzing a chemical reaction comprising contacting a reactant or reactants of said chemical reaction with a substantially plane slab of a material having on one surface one or more indents of a depth approximately 5 to 20 times a roughness of said surface and a width approximately 5 to 15 times said depth.

The present invention additionally provides a method for treating a human or animal subject having a disease comprising contacting said subject with a substantially plane slab of a material having on one surface one or more indents of a depth approximately 5 to 20 times a roughness of said surface and a width approximately 5 to 15 times said depth.

In a further embodiment said disease is caused by a virus, bacterium or fungus

The present invention additionally provides a method for killing a pest of an animal or plant comprising contacting said animal or plant with a substantially plane slab of a material having on one surface one or more indents of a depth approximately 5 to 20 times a roughness of said surface and a width approximately 5 to 15 times said depth.

The present invention additionally provides a method for killing a plant comprising contacting said plant with a substantially plane slab of a material having on one surface one or more indents of a depth approximately 5 to 20 times a roughness of said surface and a width approximately 5 to 15 times said depth.

In a further embodiment one or more additional agents are immobilized or adsorbed onto a surface opposite the indented surface. The agents may comprise one or more biocatalyst agents.

The present invention additionally provides a formulation of matter comprising: (a) a substantially plane slab of a material having on one surface one or more indents of a depth approximately 5 to 20 times a roughness of said surface and a width approximately 5 to 15 times said depth; (b) excipients, additives, stabilizers or other agents.

A technical advantage of the present invention is that it promotes the transfer of electrons across a potential barrier, and for a particular energy barrier that exists on the border between a solid body and a vacuum, provides a surface with a sharply defined geometric pattern that causes destructive interference between reflected electron probability waves (De Broglie waves). Another technical advantage of the present invention is that it allows for an increase in particle emission through a potential energy barrier. Another technical advantage of the present invention is that a surface has a sharply defined geometric pattern of a dimension that promotes destructive interference of the reflected elementary particle probability waves.

The present invention is concerned with the use of materials having nano-structured features as catalysts.

The present invention is concerned with the use of materials having nano-structured features as sensors.

The present invention is concerned with the use of materials having nano-structured features as agents to increase the biological activity of enzymes, antibodies, receptors, proteins and the like.

The present invention is concerned with the use of materials having nano-structured features as agents to reduce the biological activity of enzymes, antibodies, receptors, proteins and the like.

The present invention is concerned with the use of materials having nano-structured features, either alone or in conjunction with another agent, as biosensors.

The present invention is concerned with the use of materials having nano-structured features, either alone or in conjunction with another agent, as pesticides.

The present invention is concerned with the use of materials having nano-structured features, either alone or in conjunction with another agent, as herbicides.

The present invention is concerned with the use of materials having nano-structured features, either alone or in conjunction with another agent, as therapeutic agents for humans or animals.

BRIEF DESCRIPTION OF THE SEVERAL VIEWS OF THE DRAWING

For a more complete understanding of the present invention and the technical advantages thereof, reference is made to the following description taken with the accompanying drawings, in which.

DETAILED DESCRIPTION OF THE INVENTION

Figure 1:
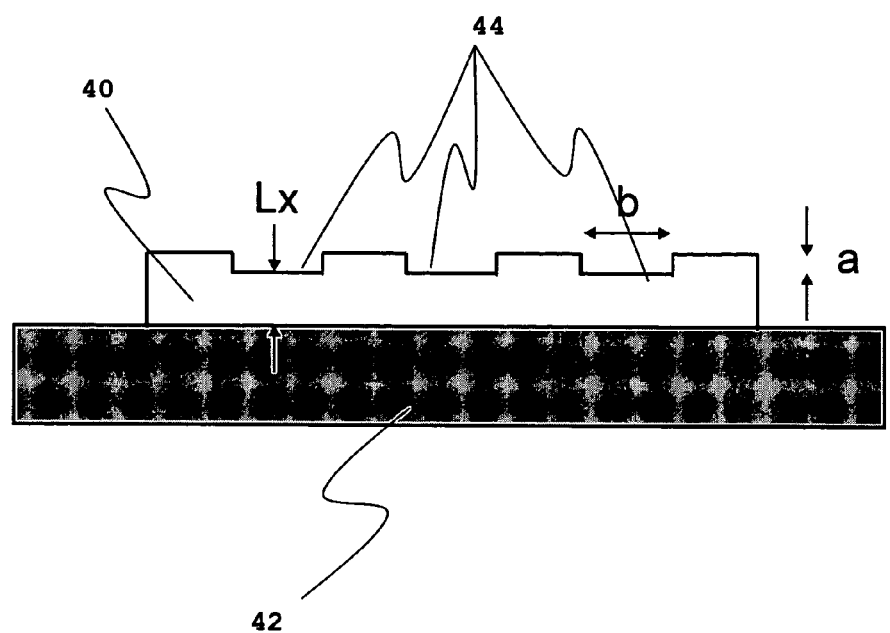
FIG. 1 is a diagrammatic representation of a possible realization with indented wall. Indents are etched on the surface of thin film deposited on insulating substrate.
Figure 2:
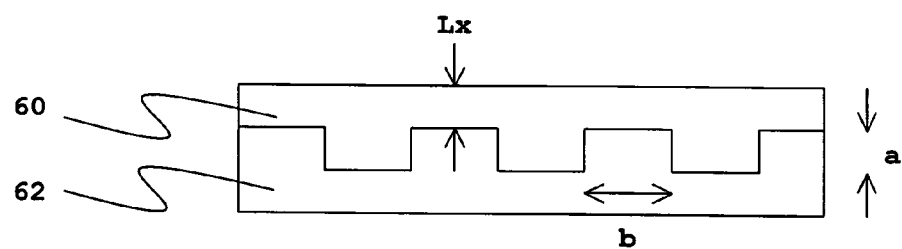
FIG. 2 is a diagrammatic representation of a possible realization of material with indented wall. Indents are etched on the surface of an insulating substrate, on which is deposited a thin film.

The embodiments of the present invention and its technical advantages are best understood by referring to FIGS. 1-2. In the following, the term "nano-structured surface" is to be understood to mean a surface of the type shown in FIGS. 1-2 and described below.

Referring now to FIG. 1, a thin film 40 is deposited on substrate 42, and indents 44 are formed in the film. Indents have depth a and width b. Thus the film resembles a corrugated pattern of squared-off, "u"-shaped ridges and/or valleys. Alternatively, the pattern may be a regular pattern of rectangular "plateaus" or "holes," where the pattern resembles a checkerboard. The walls of indent 64 should be substantially perpendicular to one another, and its edges should be substantially sharp. The surface configuration comprises a a substantially plane slab of a material having on one surface one or more indents of a depth approximately 5 to 20 times a roughness of said surface and a width approximately 5 to 15 times said depth. The walls of the indents are substantially perpendicular to one another, and the edges of the indents are substantially sharp. Typically the depth of the indents is $\geqq \lambda/2$, wherein $\lambda$ is the de Broglie wavelength, and the depth is greater than the surface roughness of the surface. Typically the width of the indents is $>>\lambda$, wherein $\lambda$ is the de Broglie wavelength. Typically the thickness of the surface is a multiple of the depth, preferably between 5 and 15 times said depth, and preferably in the range 15 to 75 nm.

The introduction of grooves into a surface as illustrated in FIG. 1 reduces the electron volt work function of the material. This physical characteristic has been observed qualitatively using PEEM microscopy and measured quantitatively using a Kelvin probe.

Referring now to FIG. 2, a thin film 60 is deposited on a structured substrate 62. The structured substrate as indentations of depth a and the distance between the indents is b. This means that the film has thickness $L_x$ and has indents of depth a and width b, but now the active surface is plane. In one embodiment the present invention is a catalyst, in which the flat surface shown in FIG. 2 can be disposed in a region enclosing reactant molecules. The molecules may be present in gaseous, liquid or plasma phase, and enclosed in any reaction vessel or tube commonly used in the art. In one embodiment of the present invention, the flat surface is conveniently formed on a macroscopic substrate, to allow easy positioning of the catalyst within the enclosure. For example, the enclosure may form the catalytic converter of an automobile. A typical converter uses two different types of catalysts, a reduction catalyst and an oxidization catalyst. The reduction catalyst uses platinum and rhodium to help reduce the NOx emissions, and the oxidation catalyst reduces the unburned hydrocarbons and carbon monoxide by burning (oxidizing) them over a platinum and palladium catalyst. Both the reduction and oxidation catalysts may be replaced by a catalyst of the present invention. In another embodiment of the present invention, the flat surface is formed on the surface of a nano-structured particle, which allows for the catalyst material to be added directly to the reaction mixture, thereby reducing or eliminating the rate limiting mass action requirements of conventional heterogenous catalysis. The nanostructured particle may be formed by granulating or otherwise breaking into particles of size up to 1 micron.

In a further embodiment the surface shown in FIG. 2 may have further materials attached to it. The properties of any molecule are highly dependent upon the context in which they are situated. This requires that great care be taken with the adsorption of molecules to a nano-structured surface, as the event of association with the nano-structured surface may render the adsorbed molecules non-functional. Adsorption of a molecule onto the surface disclosed in FIG. 2 might be carried out directly, through non-covalent associations involving local charge distributions and van der waals forces, or facilitated through association with a deposited substrate on the surface. The facilitated adsorption of a molecule to a nano-structured surface might be achieved with a chemical tag or agent arrayed on the nano-structured surface that has suitable counterpart attached to the nano-structured surface of the molecule to be adsorbed. A commonly used method for attaching biomolecules such as proteins, nucleic acids and the like is the biotin-streptavidin binding pair. In this embodiment spots of streptavidin are arrayed on the nano-structured surface to serve as a capture agent for a biotinylated molecule. Thus a reducing agent associated with a nano-structured surface will require less energy to carry out a given redox reaction. If a given biological mechanism, such as the regulation the opening of an ion channel is regulated by molecules with redox activity, the association of the regulatory molecule with the nano-structured surface is likely to cause a change in the potentiation of the opening or closing of the channel, depending on the requirement for opening and closing. It is impossible to predict what effect, if any, the association of an on the binding of a ligand to a receptor which induces a conformational change, or otherwise transduces a signal through conformational and not chemical characteristics. However, even if the effect of a particular AM-biomolecule on a cell is toxic, there are potential applications that may be developed using the as an antimicrobial agent in agricultural and industrial, if not medical applications.

In a further embodiment the present invention is a sensor. Sensors detect the presence of a particular material by the perturbation in local conditions when a molecule to be sensed interacts with the sensor surface. The perturbation in local conditions may be an electrical change as a result of a redox reaction with a material coating the surface, or it may be a change in the surface plasmon resonance as a result of the interaction event. In the present invention, the sensor surface has the nano-structured surface described in the foregoing. The interaction of the material to be sensed with the sensor surface causes a change in the wave interference behavior of the electrons comprising the sensor surface. The change in the wave interference behavior of the sensor surface may be detected, for example, by measuring, directly or indirectly, a change in the work function of the material.

In a further embodiment the present invention is a biosensor. Biosensors generally comprise one or more biological molecules or entities in electrical contact with a sensor surface. The biological molecule may, for example, be an enzyme, protein, receptor, antibody, hapten or nucleic acid molecule. The biological entity may be a cell or organelle. Biosensors detect the presence of a particular material by the perturbation in local conditions when a molecule to be sensed interacts with the biological molecule or entity. The perturbation in local conditions may be an electrical change as a result of a redox reaction, or it may be a change in the surface plasmon resonance as a result of the binding event. In the present invention, the sensor surface has the nano-structured surface described in the foregoing. The interaction of the material to be sensed with the one or more biological molecules causes a change in the wave interference behavior of the electrons comprising the sensor surface. The change in the wave interference behavior of the sensor surface may be detected, for example, by measuring, directly or indirectly, a change in the work function of the material. Alternatively, the movement of electrons from the nano-structured surface is connected to an electronic monitoring device that is sensitive to a long-term change in the electron flow from the nano-structured surface. It is likely that a stable interaction between a nano-structured surface and a biomolecule will induce such a long-term change in the electron flow from the nano-structured surface. The specificity of this interaction is achieved by construction of the nano-structured surface that is presenting an antibody or analogous binding partner for a specific biomolecule. Once constructed, the basic biosensor might then be implemented in several ways.

For example, the nano-structured surface biosensor is electrically connected to a drug delivery system. Such a sensor will be engineered to detect for example, the presence of a specific microbe; or in another example, a change in the chemical environment (e.g. the presence of hyperglycemic levels of glucose). Upon sensing the specific condition, the monitoring device would release specific amounts of a drug that is contained within the device. Upon drug distribution, there should be a signal broadcast that is detected by a receiver outside of the body. Depending on the scale of such a device, this application might be used for either single-shot emergency purposes, or for treatment of a chronic medical condition. If used on an ongoing basis, (not all stored drug is released simultaneously), a mechanism must be developed to reset or regulate the system. One limitation of this application would be the amount of drug required to be stored in such a device, and the need to refill the drug compartment. However, this might be reduced if the drug is associated with an nano-structured surface, thereby increasing its activity and lowering the required dose (see above).

A biosensor of the present invention may be applied to portable and stationary detectors of biological and chemical weapons. According to this embodiment a device that inputs an air sample over a series of biosensors that are each specific to a given agent. The required size of the device would vary with the volume of air/second that is required to be monitored. The smallest version of such a device would be portable and hand-held or easily installed into a standard car, allowing for wide distribution among police and other security personnel and enabling a timely response upon hazard detection. Such a device would also be useful on commercial aircraft, which are ideally suited for wide distribution of pathogens.

A biosensor of the present invention may be applied to water analysis. Strikingly, the current water safety measures are taken only after the water has been cultured for several hours and the microbe detected. A biosensor array of the present invention that is specific to the most common forms of bacterial contamination would decrease the length of time required for positive detection and public notification of contaminated water. The design of such a device would be very similar to that described above for biological weapons detection, with the exception that the detector composed of the nano-structured surface will be exposed to circulating water instead of air, and the specific adsorbed sensing molecules would correspond to the most common water contaminants. Another difference is that it is unlikely that the water being tested under certain circumstances is completely free from bacterial contamination. Therefore, the biosensor would have to be designed to distinguish between varying ranges of microbe titer, or at a minimum be able to distinguish between acceptable and unacceptable bacterial concentrations. As described, this device could also be utilized to guard against intentional water contamination, with the only limitation being the types of agents recognized by the nano-structured surface.

In one embodiment the present invention is a biocatalyst, in which the flat surface shown in FIG. 2 is shown as being disposed in a region enclosing reactant molecules. Enzyme molecules are absorbed onto the surface. The molecules may be present in gaseous or liquid phase, and enclosed in any reaction vessel or tube commonly used in the art. In one embodiment of the present invention, the surface is conveniently formed on a macroscopic substrate, to allow easy positioning within the enclosure. Where the enzyme catalyses a redox reaction, then the close proximity of the enzyme to the surface of the invention, or its absorbtion thereto, further enhances the activity of the enzyme by reducing the work needed to be done to transfer electrons between the enzyme and the surface. Thus an embodiment of the present invention is an enzyme immobilized or adsorbed onto a nano-particulate form of the surface of the invention. Such an enzyme preparation will have enhanced properties, and be useful in high-value biotransformations and stereo-specific and regio-specific synthesis.

In one embodiment the present invention is a biological agent having modified properties, in which the flat surface shown in FIG. 2 is shown as being disposed in a region enclosing reactant molecules. Binding molecules are absorbed onto the surface, such as an antibody, a receptor or a nucleic acid molecule. The association of the binding molecule with the nano-structured surface of the present invention changes the binding properties. This is a particularly useful feature in immunoassays and gene probe-based assays, leading either to an increase in binding affinity, and increase in specificity, or an increase in detectability. This is also particularly useful where the binding molecule is useful as a drug, either for an application like antibody-directed pro-drug therapy, anti-tumor treatments or other ameliorative applications of biological agents as therapeutics, or herbicides or pesticides, and as a antibacterial, antifungal or antiviral agent.

Additionally, the binding molecule may be used to bring the nano-structured surface of the present invention into close proximity to a therapeutic target. Thus, where the therapeutic target is a cancer cell, an antibody, for example, may serve to effectively cover the surface of the cancer cell with the nano-particulate form of the surface of the invention. The properties of the surface of the invention are such as to result in the death of a cell so covered. Such an approach may be particularly useful for the treatment of cancers of the blood and lymphomas. It may also be useful in herbicides and pesticides, and as a antibacterial, antifungal or antiviral agent.

The properties of these nano-structured surfaces have the potential to accelerate and potentiate biochemistry. For example, it is possible that the activity of a therapeutic agent will be increased through its association with a nano-structured surface. In such a case, an increase in drug efficacy may allow for a marked reduction in required dosage and by extension, toxicity and deleterious side-effects. In another example, an ineffective candidate drug may become effective through an association with the nano-structured surface, thereby increasing the pool of candidates that may be biologically acceptable. Together, these scenarios suggest that these nano-structured surfaces might prove an indispensable addition to the drug development process from the earliest stages.

Use of these nano-structured surfaces in pharmaceutical applications requires the adsorption of the potential therapeutic agent to the nano-structured surface. Therefore, distribution of them for this application may be carried out in either an 'off the shelf' approach or by direct license of the patent. An 'off the shelf' nano-structured surface for drug applications would be a colloidal surface that is either ready for treatment with any given adsorption substrate, or comes pre-coated with adsorption substrate. The specific adsorption substrates to use would need to be determined through a combination of laboratory research to establish what is most useful, and through market research to determine which molecular anchors are most commonly used.

In a yet further embodiment of the present invention, the nano-structured surface itself, particularly in granulated form, may act as a herbicide or pesticide, or as a antibacterial, antifungal or antiviral agent. Coatings of other materials on the nano-structured surface may modify the raw properties of the nano-structured surface to make it more or less suitable for particular targets. In the case of bacteria, mold, and fungi, this may entail the association of an nano-structured surface with an electron donor that targets a cell membrane or cell wall receptor, introducing an unacceptable charge load in the cell. Another example of similar concept would be to associate an ion channel regulatory molecule with the nano-structured surface. The overstimulated activation/repression of the specific channel would shut down the cell, also leading to cell death. The great advantage of such a class of antimicrobials would be the ability to determine the specificity of action by the choice of the adsorbed bioactive molecule. Nano-structured surface antimicrobials could be used similarly to antibiotics, and will become increasingly important as microbial antibiotic resistance increases. In all cases, the nano-structured surface antimicrobial and pesticide should be in such a form that it can be sprayed onto fields with the same equipment currently used for standard chemical pesticides.

Although the above specification contains many specificities, these should not be construed as limiting the scope of the invention but as merely providing illustrations of some of the presently preferred embodiments of this invention.

Indentations and protrusions to a basic surface are both described in the specification, and there is really little technical difference between the two, except in their production method. Where an indented surface is referred to, it should be read as also referring to a surface having protrusions, which, by definition, causes the surface to have an indented cross-section, having indents in the 'spaces' between the protrusions.

The method for enhancing passage of elementary particles through a potential barrier has many applications as disclosed in the foregoing.

The invention claimed is:

1. A method for catalyzing a chemical reaction comprising contacting a reactant or reactants of said chemical reaction with a substantially plane slab of a material having on one surface one or more indents of a depth approximately 5 to 20 times a roughness of said surface and a width approximately 5 to 15 times said depth.

2. The method of claim 1 wherein one or more additional agents are immobilized or adsorbed onto a surface opposite said one surface.

3. The method of claim 1 wherein one or more additional biocatalyst agents are immobilized or adsorbed onto a surface opposite said one surface.

4. A method for treating a human or animal subject having a disease comprising contacting said subject with a substantially plane slab of a material having on one surface one or more indents of a depth approximately 5 to 20 times a roughness of said surface and a width approximately 5 to 15 times said depth.

5. The method of claim 4 wherein one or more additional agents are immobilized or adsorbed onto a surface opposite said one surface.

6. The method of claim 4 wherein one or more additional biocatalyst agents are immobilized or adsorbed onto a surface opposite said one surface.

7. The method of claim 4 wherein said disease is caused by a virus, bacterium or fungus.

8. A method for killing a pest of an animal or plant comprising contacting said animal or plant with a substantially plane slab of a material having on one surface one or more indents of a depth approximately 5 to 20 times a roughness of said surface and a width approximately 5 to 15 times said depth.

9. The method of claim 8 wherein one or more additional agents are immobilized or adsorbed onto a surface opposite said one surface.

10. The method of claim 8 wherein one or more additional biocatalyst agents are immobilized or adsorbed onto a surface opposite said one surface.

11. A method for killing a plant comprising contacting said plant with a substantially plane slab of a material having on one surface one or more indents of a depth approximately 5 to 20 times a roughness of said surface and a width approximately 5 to 15 times said depth.

12. The method of claim 11 wherein one or more additional agents are immobilized or adsorbed onto a surface opposite said one surface.

13. The method of claim 11 wherein one or more additional biocatalyst agents are immobilized or adsorbed onto a surface opposite said one surface.

* * * * *